Figure 1:
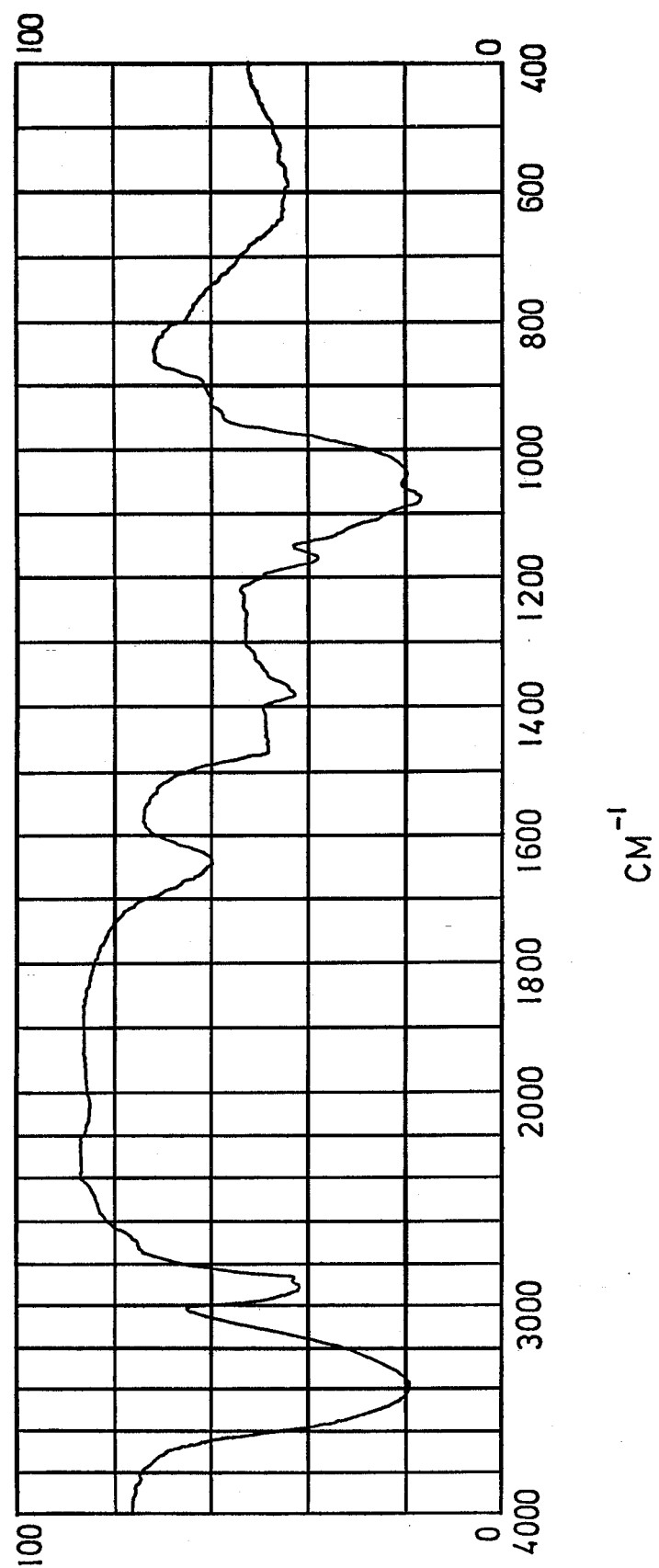

United States Patent

Takemoto et al.

[11] 4,084,010
[45] Apr. 11, 1978

[54] GLYCOSIDES HAVING SWEETNESS

[75] Inventors: Tsunematsu Takemoto, Tokushima; Tadashi Nakajima, Takatsuki; Shigenobu Arihara, Tokushima; Megumi Okuhira, Ibaraki, all of Japan

[73] Assignees: Tsunematsu Takemoto, Tokushima; Nippon Shoji Kaisha, Ltd., Osaka, both of Japan

[21] Appl. No.: 755,425

[22] Filed: Dec. 29, 1976

[30] Foreign Application Priority Data

Jan. 1, 1976   Japan ............................ 51-001233
Sep. 9, 1976   Japan ............................ 51-108499

[51] Int. Cl.$^2$ .......................... A23L 1/22; C07J 17/00
[52] U.S. Cl. ......................................... 426/548; 536/5
[58] Field of Search .................. 536/5, 6, 7; 426/548; 260/397.2

[56] References Cited

PUBLICATIONS

Wall et al, "Sterodial Sapogenins" Chemistry, Feb. 7, 1952, pp. 533–537.
Percival et al, "Structural Carbohydrate Chem." Muller Ltd. Inc, London 1953, pp. 112 & 203.

Primary Examiner—Natalie Trousof
Assistant Examiner—Cary Owens
Attorney, Agent, or Firm—Stevens, Davis, Miller & Mosher

[57] ABSTRACT

Glycosides having an excellent sweetness and hydrolysate thereof of the formula:

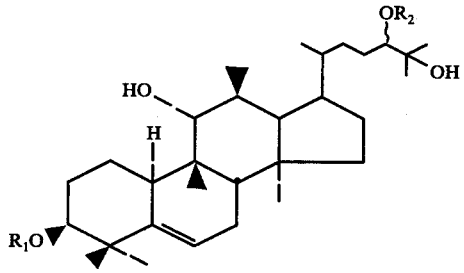

wherein $R_1$ and $R_2$ are the same or different and are each hydrogen, a residue of $\beta$-D-glucose, or a residue of an oligosaccharide comprising not more than four D-glucose having 1,2-, 1,4- and/or 1,6-bond, provided that the total number of D-glucose residue in $R_1$ and $R_2$ is not more than 6, which is isolated from a fruit of a plant of Cucurbitaceae, particularly Momordica grosvenori Swingle (e.g. Fructus Momordicae) and said hydrolysates are produced by hydrolyzing the glycosides with an enzyme.

9 Claims, 14 Drawing Figures

P: $Py-d_5$    H: HOD

P: Py-d₅   H: HOD

P: Py-d₅   H: HOD

P: Py-d₅    H: HOD

P: Py-d₅    H: HOD

GLYCOSIDES HAVING SWEETNESS

The present invention relates to novel glycosides having an excellent sweetness which are isolated from a plant of *Cucurbitaceae* and hydrolysates thereof. More particularly, it relates to glycosides wherein the non-sugar component is a triterpene alcohol and the sugar component is a glucose, which is isolated from a fruit of *Momordica grosvenori* Swingle which is a perennial herb of *Cucurbitaceae*, hydrolysates derived from he glycosides, and a sweetening agent comprising the compounds.

The Momordica grosvenori Swingle of a perennial herb of *Cucurbitaceae* is cultured at a mountainous district in Southern China, and the crude drug obtained from the fruit is called as "Fructus Momordicae", which has been widely used as a folk medicine for analgesic, expectorant, antitussive, treatment of infiltration of the lungs, or as a material for a refreshing drink, or as a seasoning for foods.

This Fructus Momordicae has a good sweetness and it has been reported in a chinese literature that this crude drug contains a large amount of glucose.

As the results of the present inventors' extensive study on the various components, particularly the sweetening components, of Fructus Momordicae, it has been found that one of the components having excellent sweetness is fructose but is not glucose. However, the content of the fructose is merely about 14 to 15%, and hence, it is assumed that the sweetness of Fructus Momordicae is not merely owing to this sugar component, but other sweetening component should be contained. As the result of further extensive study, it has been found that the most important sweetening component is some saponin glycosides wherein the non-sugar component is a triterpene alcohol and the sugar component is glucose, and then the glycosides have been successively isolated from the crude drug and some hydolysates have been derived therefrom.

Recently, it has been reported by Chi-Hang Lee that an extract from Momordicae grosvenori with water of 50% ethanol shows an excellent sweetness and the sweetener component is a glycoside of a triterpenoid [Experientia, Vol. 31, page 533 (1975)], but he did neither isolate the active component nor determine the precise chemical structure thereof.

An object of the present invention is to provide a novel glycoside isolated from a fruit of a plant of Cucurbitaceae.

Another object of the invention is to provide a hydrolysate derived from the glycoside.

A further object of the invention is to provide a process for producing the glycoside or hydrolysate thereof.

A still further object of the invention is to provide a sweetening agent comprising the glycoside or hydrolysate thereof.

These and other objects of the invention will be apparent from the following description.

The glycosides and hydrolysates thereof of the present invention have the following formula:

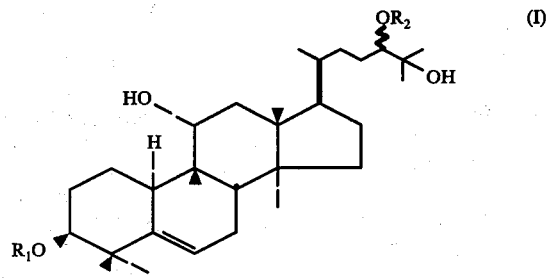

wherein $R_1$ and $R_2$ are the same or different and are each hydrogen, a residue of β-D-glucose, or a residue of an oligosaccharide comprising not more than four D-glucoses having 1,2-, 1,4- and/or 1,6-bond, provided that the total number of D-glucose residue in $R_1$ and $R_2$ is not more than 6.

Preferred compounds are the compounds of the formula (I) wherein $R_1$ and $R_2$ are the same or different and are each a residue of an oligosaccharide comprising not more than four β-D-glucoses having 1,2-, 1,4- and/or 1,6-bond and the total number of D-glucose is five or six; $R_1$ is a residue of an oligosaccharide comprising two β-D-glucoses having 1,6-bond and $R_2$ is a residue of an oligosaccharide comprising two β-D-glucoses having 1,2-bond; $R_1$ is a residue of β-D-glucose and $R_2$ is a residue of an oligosaccharide comprising two β-D-glycoses having 1,2-bond; $R_1$ and $R_2$ are each a residue of β-D-glucose; $R_1$ is a residue of β-D-glucose and $R_2$ is hydrogen; and $R_1$ and $R_2$ are each hydrogen.

Particularly preferred compounds are the compounds of the formula (I) wherein $R_1$ is 6-(1-β-D-glucopyranosyl)-β-D-glucopyranosyl and $R_2$ is 2,6-bis(1-β-D-glucopyranosyl)-β-D-glucopyranosyl (hereinafter, referred to as "S-5"); $R_1$ is 6-(1-β-D-glucopyranosyl)-β-D-glucopyranosyl and $R_2$ is 2-(1-β-D-glucopyranosyl)-β-D-glucopyranosyl (hereinafter, referred to as "S-4"); and $R_1$ and $R_2$ are each a residue of an oligosaccharide comprising not more than four β-D-glucoses having β-1,2-, β-1,4- and/or β-1,6-bond and the total number of the glucose residue in $R_1$ and $R_2$ is six (hereinafter, referred to as "S-6"), which are isolated from Fructus Momordicae and have an excellent sweetness.

Another preferred compounds are the compounds of the formula (I) wherein $R_1$ is 1-β-D-glucopyranosyl and $R_2$ is 2-(1-β-D-glucopyranosyl)-β-D-glucopyranosyl (hereinafter, referred to as "S-3"); $R_1$ and $R_2$ are each 1-β-D-glucopyranosyl (hereinafter, referred to as "S-2"); and $R_1$ is 1-β-D-glucopyranosyl and $R_2$ is hydrogen (hereinafter, referred to as "S-1"), which is produced by hydrolysing the above S-4, S-5 or S-6 and is useful as an intermediate for preparing a compound having an excellent sweetness, while it has a week sweetness.

The glycosides of the present invention have a similar structure of natural glycosides and the sugar component is β-bonded with the non-sugar component at 1-position of the terminal glucose. In the specification, the term "residue" means the group derived from glucose or oligosaccharides by removing one hydroxy group therefrom. The chemical name "6-(1-β-D-glucopyranosyl)-β-D-glucopyranosyl" used for $R_1$ and $R_2$ may alternatively be named as "β-D-glucopyranosyl(1→6)-β-D-glucopyranosyl". Likewise, "2,6-bis(1-β-D-glucopyranosyl)-β-D-glucopyranosyl"

may alternatively be named as "β-D-glucopyranosyl(1→2)-[β-D-glucopyranosyl(1→6)]-β-D-glucopyransoyl".

According to the present invention, the glycosides can be obtained from the fruit of a plant of *Cucurbitaceae* by extracting with an appropriate polar solvent, such as water, lower alcohols (e.g. methanol or ethanol) at room temperature. The desired compounds can not be extracted with petroleum ether, ethyl ether, ethyl acetate, etc. The starting fruit may optionally be defatted before the extraction. The extract thus obtained contains a large amount of fructose and other impurities in addition to the desired sweentening components.

The extract is then concentrated and dissolved in a small amount of water. The aqueous solution is washed with ethyl ether and etyl acetate. The aqueous layer is adsorbed onto active carbon and eluted with pyridine. Alternatively, the aqueous layer is treated with a synthetic adsorbent (e.g. Amberlite XAD-2) and eluted with methanol; or is treated with Cephadex and a solution of the fraction thus obtained in methanol is passed through an activated alumina column and eluted with methanol-water (1 : 1 by volume). The eluate thus obtained is concentrated to give slightly colored powdery materials having excellent sweetness with a slightly bitter taste. The materials are subjected to a silica gel thin layer chromatography (hereinafter, referred to merely as "TLC") wherein n-butanol-acetic acid-water (4: 1 : 1 by volume) is used as a developer. As the result, the materials comprises mainly three components. The materials are subjected to a silica gel column chromatography, and thereby, they are separated into three components: i.e. a component having a largest Rf value on the above TLC (which corresponds to S-4), a component having a middle Rf value on TLC (which corresponds to S-5), and a component having smallest Rf value on TLC (which corresponds to S-6).

In preferred embodiment, the S-4, S-5, and S-6 components can be isolated from Fructus momordicae in the following manner.

Fructus momordicae is ground with a mixer and extracted with a 50% aqueous methanol with heating. The extract is concentrated under reduced pressure. The resulting brown viscous material is dissolved in a small amount of water, washed with ethyl ether and ethyl acetate (each twice). The aqueous layer having a sweetness is concentrated under reduced pressure to give a brown viscous extract. The extract is dissolved in an appropriate amount of water and is adsorbed onto active carbon with stirring at room temperature for several hours. The active carbon adsorbed with the components is washed with water until the washing liquid shows no more sweetness, and then, the component is eluted with a 99% ethanol and further with pyridine. These eluates are each concentrated under reduced pressure. As the result, the pyridine fraction contains sweetening components while no fructose is contained. It is confirmed by TLC that the pyridine fraction contains several components. The pyridine fraction is dissolved in a small amount of methanol and is passed through a previously prepared an activated alumina column and developed with methanol. After washing well the column with methanol, the adsorbed components are eluted with methanol-water (1 : 1 by volume). The eluate is concentrated under reduced pressure to give powdery materials containing said three components. The materials thus obtained are adsorbed onto about three times amount of Celite 535 (a tradename of diatomaceous earth made by Johns Manville Sales). The resultant is introduced into a silica gel column and developed with chloroform and then eluted with a mixed solvent of chloroform-methanol. Referring to the test result with TLC, the silica gel chromatography is repeated to isolate the desired components.

Figure 2:
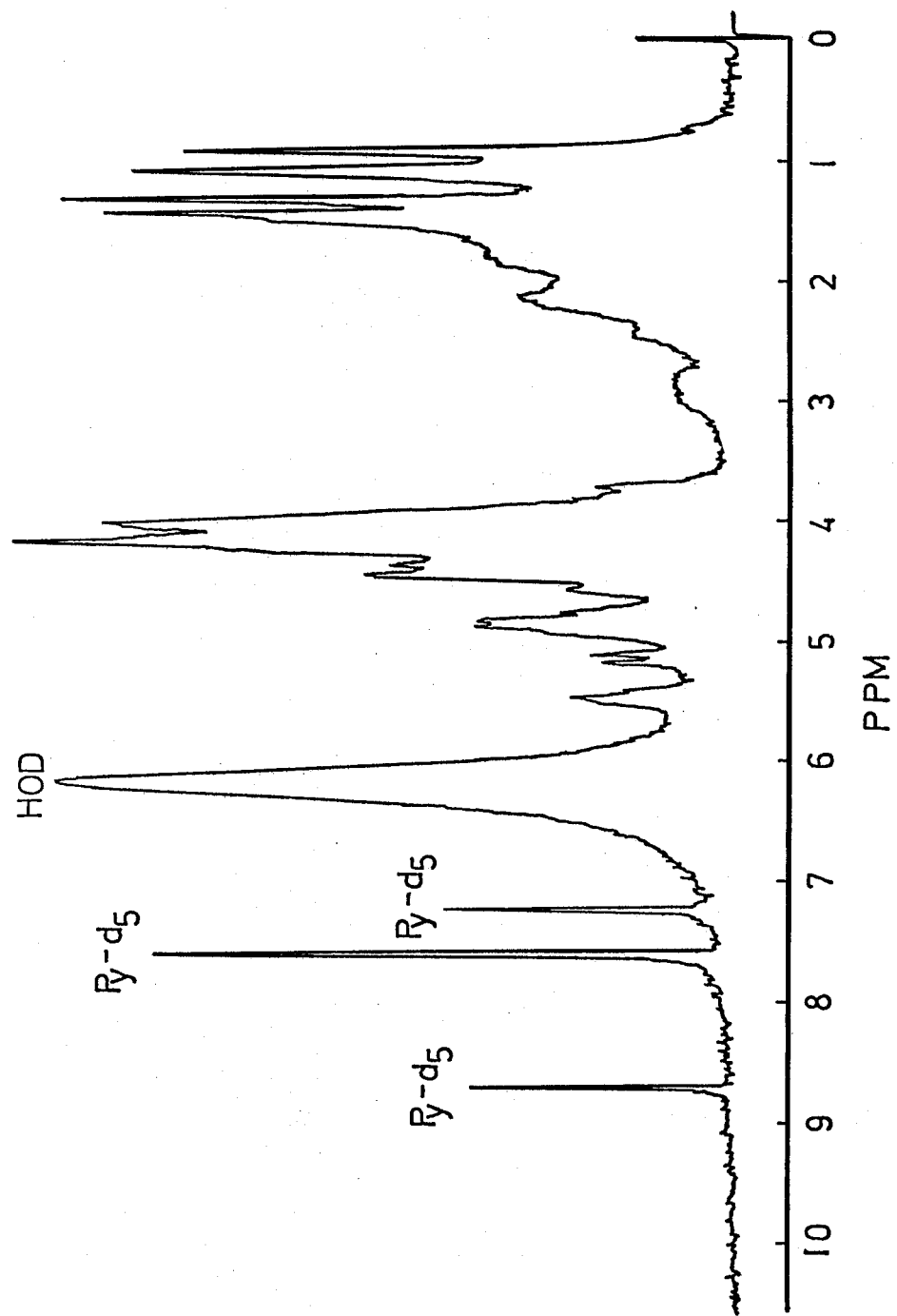

S-5 is a powdery substance having a good and strong sweetness, melting point (not corrected): 197° - 201° C (decomp.), $[\alpha]_D^{20}$ −9.4° ($H_2O$), elementally analysis for $C_{60}H_{102}O_{29}·2H_2O$: Found (%): C, 53.90; H, 8.01; hydrate, 2.4. The infrared spectrum and NMR spectrum thereof are shown in the accompanying FIGS. 1 and 2, respectively. This substance is soluble in water, methanol, ethanol and pyridine and is insoluble in petroleum ether, ethyl ether and ethyl acetate. The 0.02% aqueous solution of S-5 is about 260 times sweeter than fructose and has a sweetness similar or more excellent to that of stevioside isolated from leaves of Stevia plant which has been considered to be about 300 times sweeter than fructose.

Figure 3:
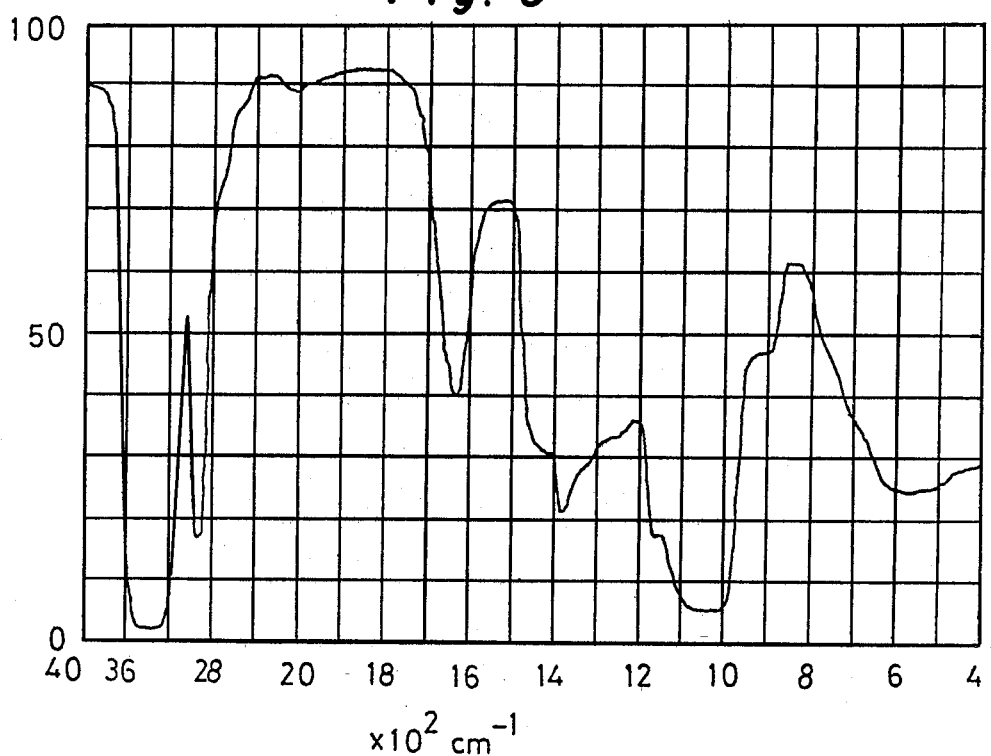
Figure 4:
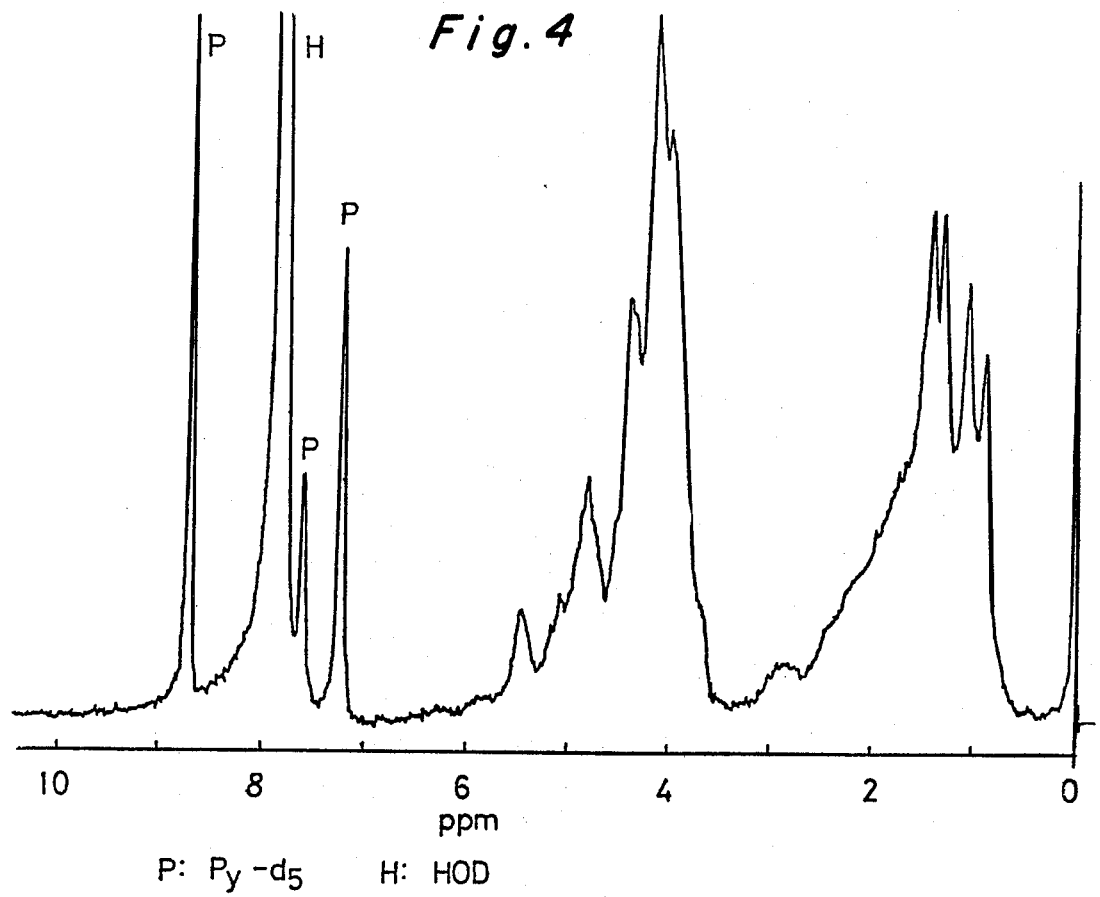

S-6 is a colorless powdery substance having a good and strong sweetness, melting point (not corrected): 198° - 204° C (decomp.), $[\alpha]_D^{29}$ −4.2° (c=1.24, methanol), elementally analysis for $C_{66}H_{112}O_{34}$: Found (%): C, 54.64; H, 7.79. The infrared spectrum and NMR spectrum thereof are shown in FIGS. 3 and 4, respectively. This substance is soluble in water, methanol and pyridine and is insoluble in petroleum ether, ethyl ether and ethyl acetate. The 0.02% aqueous solution of S-6 is about 130 times sweeter than fructose.

Figure 5:
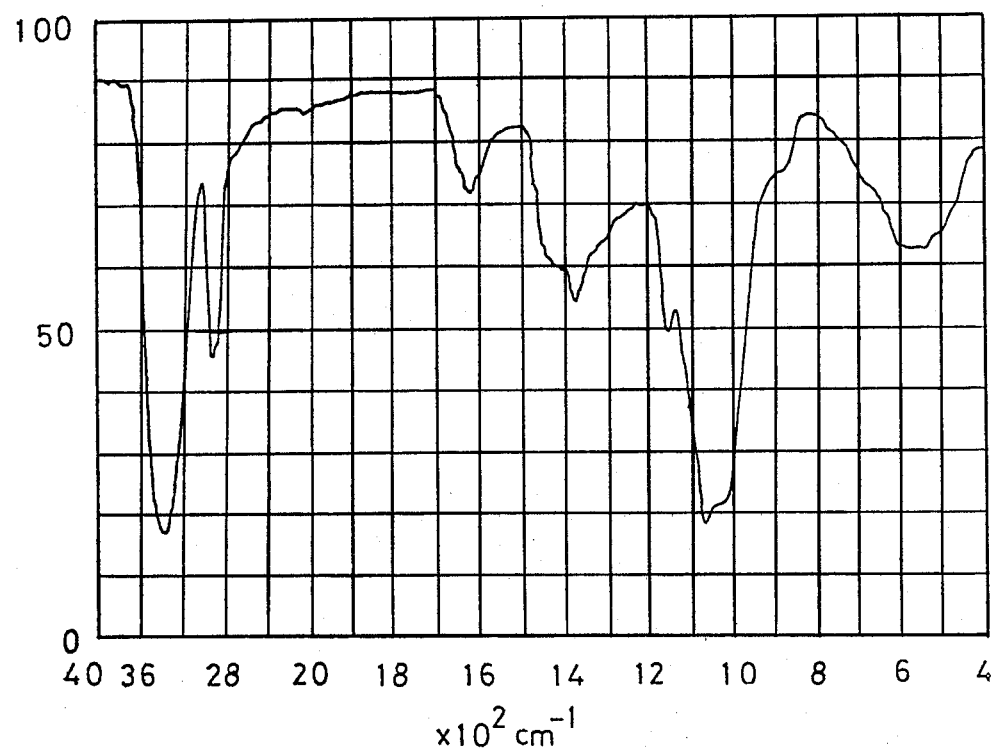
Figure 6:
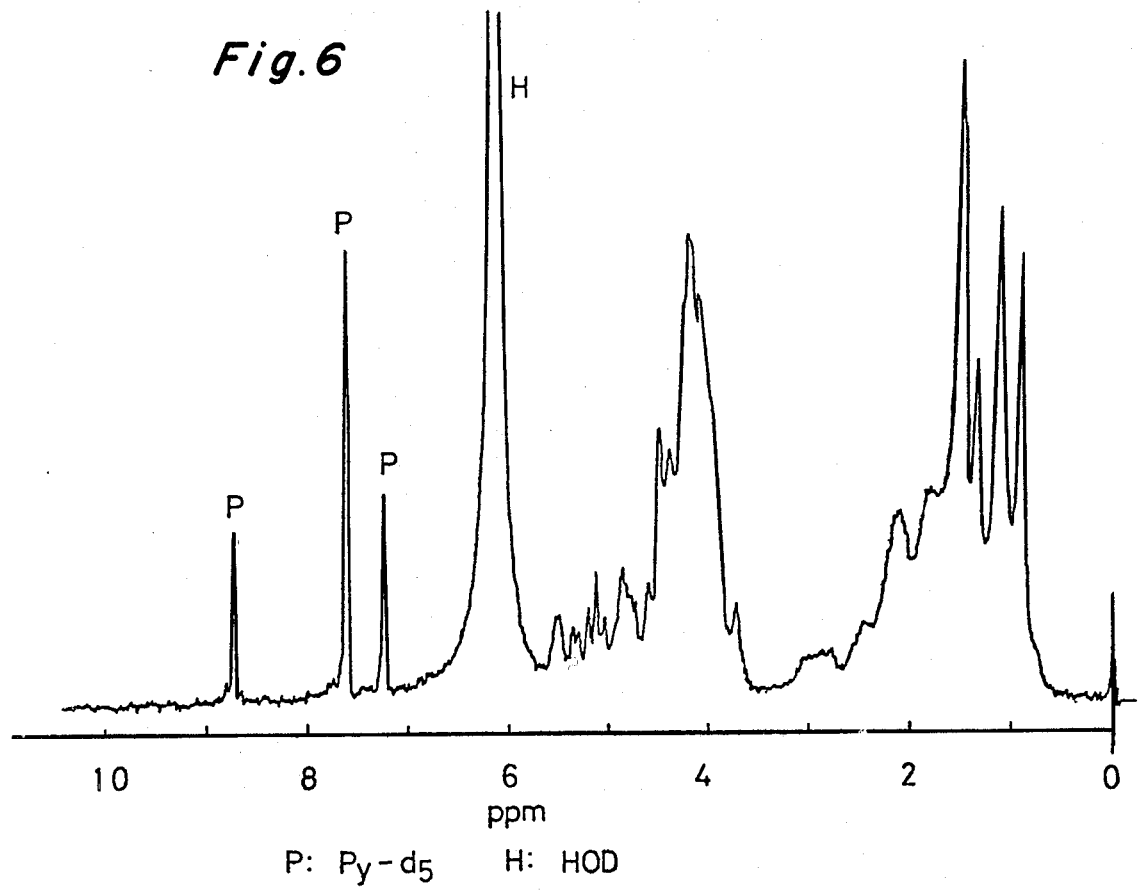

S-4 is a colorless powdery substance having a good and strong sweetness, melting point: 185° - 188° C (decomp.), $[\alpha]_D^{17}$ −4.2° (c=0.52, methanol), elementally analysis for $C_{54}H_{92}O_{24}·2H_2O$: Found (%) C, 55.47; H, 8.41. The infrared spectrum and NMR spectrum thereof are shown in FIGS. 5 and 6, respectively. This substance is soluble in water, methanol and pyridine and is insoluble in petroleum ether, ethyl ether and ethyl acetate.

The hydrolysates of the glycosides, i.e. S-1, S-2 and S-3 which have a weak sweetness with a bitter taste and S-0 which has no sweetness, are useful as an intermediate of the preparation of the compounds having an excellent sweetness, and they can be produced by hydrolysing the glycoside with an enzyme or an inorganic acid. For instance, the glycosides are dissolved in a phosphate buffer solution (pH: 3.0 - 5.0) and thereto is added maltase (optionally is further added cellulase). The mixture is reacted at about 37° - 38° C for about 2 hours to one week. The resulting hydrolysed solution is concentrated under reduced pressure and extracted with a solvent (e.g. n-butanol). The extract is concentrated under reduced pressure to give the desired hydrolysates. Alternatively, the hydrolysed solution obtained above is treated with a synthetic adsorbent (e.g. Amberlite XAD-2) and then is subjected to silica gel column chromatography. When S-5 is hydrolysed with maltase, there are produced S-3, S-2 and S-1 and also S-4 having an excellent sweetness. When S-5 is hydrolysed with maltase and subsequently with cellulase, there is produced a compound of the formula (I) wherein $R_1$ and $R_2$ are both hydrogen (hereinafter, referred to as "S-0"). Besides, when S-6, S-4, S-3 or S-2 is hydrolysed with maltase, there is produced S-1, which is hydrolysed with cellulase to give triterpene alcohol of the molecular formula: $C_{30}H_{52}O_4$ as the non-sugar component which corresponds to S-0. Moreover, when these glycosides and hydrolysates thereof are hydrolysed with an inorganic acid, S-0 is produced and also only glucose is produced as the sugar component. On the basis of these experimental results, it is confirmed that the compounds having a sweetness of the present invention are a saponin glycoside of the formula (I) wherein the non-sugar component is composed of a triterpene alcohol and the sugar component is cmposed of only D-glucose.

Thus, in one feature of the present invention, there is provided a process for producing a compound of the formula (I) wherein $R_1$ and $R_2$ are the same or different and are each hydrogen, a residue of β-D-glucose, or a residue of an oligosaccharide comprising not more than four D-glucoses having 1,2-, 1,4- and/or 1,6-bond, provided that the total number of the D-glucose residue in $R_1$ and $R_2$ is not more than 6, which comprises extracting a fruit of a plant of *Cucurbitaceae* with a polar solvent selected from the group consisting of water, methanol, ethanol and a mixture thereof, removing impurities (e.g. flavonoids, amino acids, carbohydrates, etc.), and subjecting the resulting saponin rich mixture to a silica gel column chromatography, and optionally followed by hydrolysing the isolated compound.

In one preferred feature of the invention, there is provided a process for producing a compound of the formula (I) wherein $R_1$ and $R_2$ are the same or different and are each a residue of an oligosaccharide comprising not more than four D-glucoses having β-1,2-, β-1,4- and/or β-1,6-bond, provided that the total number of the D-glucose residue in $R_1$ and $R_2$ is from 4 to 6, which comprises extracting Fructus Momordicae with a solvent selected from the group consisting of water, methanol, ethanol and a mixture thereof, removing impurities (flavonoids, amino acids, carbohydrates, etc.) subjecting the resulting saponin rich mixture to a silica gel column chromatograhy and eluting the adsorbed material with a mixed solvent of chloroform-methanol having a mixed ratio of 90 : 10 to 60 : 40, preferably 80 : 20 to 70 : 30, by volume (chloroform : methanol).

In the above process, the removal of impurities from the extract is usually carried out by introducing the extract into a column of a synthetic adsorbent, such as active carbon, Amberlite XAD-2 (a tradename of a porous resin of crosslinked polystyrol made by Rohm & Haas) or Cephadex (a tradename of a dextran gel made by Pharmacia Fine Chemicals), washing the column with water, eluating the adsorbed material with pyridine or an alcohol (e.g. methanol or ethanol), (optionally, the eluate being concentrated, and the concentrated mixture being dissolved in an alcohol such as methanol or ethanol), introducing the resulting mixture into a column of activated alumina or polyamide, and eluting the adsorbed material with methanol-water. The resulting eluate is a saponin rich mixture and it is subjected to the subsequent silica gel column chromatography after concentrated.

Besides, according to the silica gel column chromatography in the above process, the desired glycoside can be eluted with a series of a mixed solvent of chloroform-methanol having a mixed ratio of from 90 : 10 to 60 : 40, preferably 80 : 20 to 70 : 30, by volume (chloroform : methanol), wherein the eluates are fractionated into several fractions and the desired glycoside can be isolated from the fraction containing the desired glycoside which is confirmed from the results of TLC and test for sweetness thereof. The desired glycoside may be isolated by a single silica gel column chromatography with careful fractionation of the eluate, but in this case, the eluate should be fractionated into a large number of fractions, which requires complicated operation and hence is not economical. Accordingly, it is preferable to roughly fractionate the eluate with the mixed solvent of chloroform-methanol into several fractions (usually 5 to 10 fractions) by one silica gel column chromatography, and to repeatedly subjecting each resulting fraction containing the desired glycoside to the silica gel column chromatography until a single spot is observed on TLC.

In another preferred feature of the invention, there is provided a process for producing a compound of the formula (I) wherein $R_1$ and $R_2$ are the same or different and are each hydrogen, a residue of D-glucose or a residue of an oligosaccharide comprising not more than three D-glucoses having β-1,2-, β-1,4- and/or β-1,6-bond, provided that the total number of the D-glucose residue in $R_1$ and $R_2$ is not more than 3, which comprising hydrolysing a compound of the formula (I) wherein $R_1$ and $R_2$ are the same or different and are each a residue of an oligosaccharide comprising not more than four D-glucoses having β-1,2-, β-1,2- and/or β-1,6-bond and the total number of the D-glucose residue in $R_1$ and $R_2$ is from 4 to 6 (e.g. S-4, S-5 and S-6) with an enzyme.

The hydrolysis of the glycoside in the above process is carried out by reacting the starting glycoside with an enzyme (e.g. maltase, β-glucosidase or hesperidinase) in a buffer solution (e.g. a phosphate buffer solution) at an optimum pH value (e.g. pH 3.0 to 5.0) at an optimum temperature (e.g. 30 to 40° C) for about 2 hours to 1 week. With the lapse of reaction time, the hydrolysis proceeds in a higher degree, i.e. from S-3 to S-1. Suitable reaction time for producing S-3, S-2 and S-1 is about 3 hours to 3 days, about 2 days to 6 days and over about 6 days, respectively, while it is variable depending on the other reaction conditions, such as the kind of enzyme, the pH value and the temperature.

In a further preferred feature of the invention, there is provided a process for producing a compound of the formula (I) wherein $R_1$ and $R_2$ are hydrogen (i.e. S-0), which comprises hydrolysing a compound of the formula (I) wherein $R_1$ and $R_2$ are the same or different and are each hydrogen, a residue of D-glucose or a residue of an oligosaccharide comprising not more tha four D-glucoses having β-1,2-, β-1,4- and/or β-1,6-bond, provided that either one of $R_1$ and $R_2$ is other than hydrogen and the total number of the D-glucose residue in $R_1$ and $R_2$ is 1 to 6, (e.g. S-1, S-2, S-3, S-4, S-5 and S-6), with an enzyme selected from the group consisting of maltase, β-glucosidase and hesperidinase and further with cellulase, or with an inorganic acid.

The hydrolysis of the starting glycoside with an enzyme is carried out by firstly treating the starting glycoside with an enzyme selected from the group consisting of maltase, β-glucosidase and hesperidinase under the same conditions as described in the above preferred feature, wherein finally hydrolysed product is S-1, and the resulting S-1 is further hydrolysed with cellulase in a buffer solution (e.g. a phosphate buffer solution) at an optimum pH value (e.g. pH 3.0 to 5.0) at an optimum temperature (e.g. 30° to 40° C) for about two hours to one week. The hydrolysis of the glycoside with an inorganic acid is carried out by treating the starting glycoside with an inorganic acid (e.g. hydrochloride acid or sulfuric acid) in an appropriate solvent (e.g. water, methanol, ethanol, dioxane, or a mixture thereof) at an elevated temperature (e.g. 60° to 100° C), preferably at a reflux temperature of the solvent, for about 3 hours to 6 hours.

The compounds of the present invention have an excellent sweetness and are very safe to human since the starting crude drug has been widely used as a folk medicine or for foods in China. Thus, the compounds of the invention are useful as a safe sweetening agent for various foods, drinks, food additives or medicines. The present compounds have a vary strong sweetness and hence is effective in a very small amount. The present compounds are used alone or in an admixture with a non-toxic solid or liquid carrier or diluent (e.g. water, lactose, starch, etc.) or in a combination with one or moe conventional sweetening agents (e.g. sugar, invert sugar, fructose, saccharin, stevioside, etc.).

The present invention is illustrated by the following Examples.

Example 1

Fructus Momordicae (44 g) is ground with a mixer and is extracted with a 50 % aqueous ethanol (300 ml) with heating on a water bath for one hour. This extraction is repeated for four times. After cooling, the combined extracts are filtered and the filtrate is concentrated under reduced pressure. The resulting brown viscous material (12.7g) is dissolved in water (100 ml) and washed with ethyl ether and ethyl acetate (each 100 ml, twice) in a separatory funnel, by which the soluble materials are removed off. The aqueous layer having a sweetness is concentrated under reduced pressure, and the resulting residue (10.1 g) is dissolved in water (200 ml) and thereto is added active carbon (20 g). The mixture is stirred and thereby the components are adsorbed onto the active carbon.

The resulting active carbon is washed with water until the washing liquid shows no more sweetness amount of water: about 800 ml) to give Fraction I. The active carbon is further eluted with a 99% ethnaol (300 ml) and then with pyridine (500 ml) to give Fraction II and Fraction III, respectively. The Fraction I, Fraction II and Fraction III are each concentrated under reduced pressure to give residues of Fraction I (2.1 g), Fraction II (0.8 g) and Fraction III (2.4 g), respectively. The residue of Fraction III contains mainly the sweetening components. It is confirmed by TLC (adsorber: silica gel, solvent: n-butanol-acetic acid-water (4 : 1 : 1 by volume), reagent for detection: 30% sulfuric acid) (hereinafter, the TLC is carried out under the same conditions) that the powdery residue of Fraction III contains various components. This residue is dissolved in methanol (10 ml) and the solution is introduced into a column (3 cm × 10 cm) filled with an actived alumina (activation degree: 1, made by Woelm Co.; 50 g). The column is washed with methanol (300 ml) and then eluted with methanol-water (1 : 1 volume, 700 ml). The eulate is concentrated under reduced pressure to give faint yellow powdery materials (0.8 g, Fraction IV). It is confirmed by TLC that this Fraction IV contains at least three components The crude materials having a sweetness are purified by a silica gel column chromatography as follows.

The crude sweetening materials (30.5 g) are covered with Celite 535 (a tradename of diatomaceous earth made by Johns Manville Sales, 50 g) and the mixture is filled into a column (4.5 cm × 409 cm) which is previously prepared by using Wako Gel C-200 (a tradenmae of silica gel made by Wako Junyaku K.K., size: 100 - 200 mesh, 300 g), developed with chloroform (2000 ml) and then eluted with mixed solvents of chloroform-methanol (the mixed ratio of the solvents is varied like 90 : 10, 80 : 20, . . . 60 : 40 by volume, as shown in the following Table 1), wherein each 0.5 liter of the solvent is used in one elution. As the result, there are obtained the fractions as shown in Table.

Table 1

| Fraction No. | Solvent (mixed ratio by volume) | Amount of fraction (liter) |
| --- | --- | --- |
| 1 | CHCl$_3$—MeOH (90 : 10) | 10.0 |
| 2 | CHCl$_3$—MeOH (80 : 20) | 10.0 |
| 3 | CHCl$_3$—MeOH (75 : 25) | 5.0 |
| 4 | CHCl$_3$—MeOH (75 " 25) | 5.0 |
| 5 | CHCl$_3$—MeOH (75 : 25) | 5.0 |
| 6 | CHCl$_3$—MeOH (75 : 25) | 2.5 |
| 7 | CHCl$_3$—MeOH (70 : 30) | 2.5 |
| 8 | CHCl$_3$—MeOH (70 : 30) | 5.0 |
| 9 | CHCl$_3$—MeOH (70 : 30) | 5.0 |
| 10 | CHCl$_3$—MeOH (60 : 40) | 5.0 |

When these fractions are tested by TLC, the Fractions 6 and 7 contain the sweetening components. These fractions are repeatedly subjected to a silica gel chromatography (two to three times) until a single spot is observed on TLC. The material having a single spot on TLC is dissolved in a small amount of methanol and the insoluble materials are removed off. The mixture is concentrated and dried to give S-5 (yield: 1%), melting point: 197 - 201° C( decomp.), $[\alpha]_D^{20}$ −9.4° (c=3.5, H$_2$O).

Elementary analysis for $C_{60}H_{102}O_{29} \cdot 2H_2O$: Calcd (%): C, 54.45; H8.07 Found (%): C,53.90; H,8.01

EXAMPLE 2

Fructus Momordicae (530 g) is ground with a mixer and is defatted with trichlene to give defatted powder (500 g). The defatted powder (500 g) is added to a 25% aqueous ethanol (3 liters) and the mixture is allowed to stand at room temperature overnight and the liquid is separated. To the residue is further added a 25% aqueous ethanol (1 liter) and the mixture is treated likewise (this process (extraction) is repeated twice, by which the resulting residue shows no more sweetness). The separated liquids (extracts) are combines and filtered. The filtrate is concentrated so as to make about 0.5 liter, and thereto is added methanol (2 liters). The mixture is stirred well at room temperature, and the insoluble materials are filtered and are washed twice with methanol (2 liters). The filtrate and the washing liquid are combined and concentrated under reduced pressure to give a brown viscous extract (136 g). This extract is dissolved in an appropriate amount of water and the solution is introduced into a column (4.5 × 40 cm) of a mixture of active carbon (80 g) and Celite 535 (160 g). Thereafter, the column is washed with water (7 liters). The solution passed through the column and the washing liquid are combined to give Fraction I. The materials adsorbed on the column are eluted with a 20% aqueous ethanol (4 liters) and then with pyridine (2 liters) to give Fraction II and Fraction III, respectively. These fractions are each concentrated under reduced pressure to give the extracts of Fraction I (94.2 g), Fraction II (6.5 g) and Fraction III (42.8 g), respectively. The extract of Fraction III has an excellent sweetness while it does not contain fructose.

In the same manner as described in Example 1, the extraction of Fraction III is dissolved in a small amount of methanol, introduced into a column (4.5 cm × 30 cm) of an activated alumina (500 g), which is washed with methanol (3 liters) and then eluted with methanol-water (1 : 1 by volume, 7 liters). The washing liquid and the eluate are each concentrated under reduced pressure to give the fraction of the washing liquid (0.3 g) and the fraction of the eluate (13.4 g). The fraction of the eluate is faint yellow powdery material having a sweetness, which is composed of the almost same components as the Fraction IV in Example 1 by TLC. This material is purified by a silica gel column chromatography in the same manner as described in Example 1 to give the desired glycoside.

EXAMPLE 3

In the same manner as described in Example 2, a defatted powder of Fructus Momordicae (500 g, which corresponds to 43 pieces of the crude Fructus Momordicae) is extracted with a 25% aqueous ethanol and the insoluble materials are removed off by treating it with methanol, and then the resultant is concentrated under reduced pressure to give a brown viscous extract (140 g). This extract is dissolved in water (1 liter) and the solution is introduced into a column (4.5 cm × 120 cm) of Amberlite XAD-2 (average particle size: 0.45 - 0.60 mm, 1.6 liters) which is previously treated with methanol. The column is washed with water (10 liters). The solution passed through the column and the washing liquid are combined to give Fraction I. The materials adsorbed on the column are eluted with a 20% aqueous methanol (4 liters) and then a 99% methanol (4 liters) to give Fraction II and Fraction III, respectively. These fraction are each concentrated under reduced pressure to give residues of Fraction I (98 g), Fraction II (4 g) and Fraction III (26 g), respectively. The crystalline powder of Fraction III (26 g) thus obtained is dissolved in methanol (300 ml) and the solution is introduced into a column (4.5 cm × 24 cm) of an activated alumina (400 g). The column is washed with methanol (1 liter). The solution passed through the column and the washing liquid are combined to give Fraction A. The materials adsorbed on the column are eluted with methanol-water (9 : 1 by volume, 2 liters) and then methanol-water (1 : 1 by volume, 10 liters) to give Fraction B and Fraction C, respectively. These fractions are each concentrated under reduced pressure to give residues of Fraction A (0.5 g), Fraction B (2.1 g) and Fraction C (12 g), respectively. The material of this Fraction C is the almost same as the material of Fraction IV in Example 1 in accordance with TLC, and is purified likewise by a silica gel chromatography to give the desired glycoside.

EXAMPLE 4

The glycoside obtained in the above Examples was tested on the sweetness thereof as follows:

There were prepared a series of a standard sweetening agent: i.e. five series of an aqueous solution of fructose (2 g/100 ml, 3 g/100 ml, 4 g/100 ml, 5 g/100 ml and 6 g/100 ml). Separately, aqueous solutions of the glycoside (S-5) of the present invention (7.7 mg/100 ml and 20 mg/100 ml) were prepared. Moreover, as a reference, there were prepared aqueous solutions of stevioside (sold by Ogi Shoten K.K.) (10 mg/100 ml and 20 mg/100 ml).

The sweetness of the aqueous solution of S-5 and of stevioside was determined in comparison with that of the aqueous solution of fructose by using 11 panels, by which it was determined that the sweetness of the test solution corresponds to which series of the fructose solution. On the basis of the results, there were calculated the concentration of the test materials which showed the same sweetness as that of fructose (Relative to fructose value) and further the fold of sweetness of the test materials to that of fructose. The results are shown in the following Table 2.

Table 2

| Aqueous solution of sweetening materials | | Relative to fructose value of the test materials | The fold of sweetness of the test material to that of fructose |
|---|---|---|---|
| Gylycoside of the present invention (S-5) | 7.7 mg/100 ml | 2.65 | 344 |
| | 20 mg/100 ml | 5.11 | 255 |
| Stevioside | 10 mg/100 ml | 2.26 | 226 |
| | 20 mg/100 ml | 4.66 | 233 |

EXAMPLE 5

To a fine powder of Fructus Momordicae (500 g, which corresponds to 40 pieces of the crude Fructus Momordicae) is added water (5 liters) and the mixture is allowed to stand at room temperature overnight. The extract is separated, and the residue is further twice extracted with water (5 liters) (the resulting residue does almost not show a sweetness). The extracts are combined and filtered with a diatomaceous earth. The filtrate is introduced into a column (4.5 cm × 120 cm) of Amberlite XAD-2 (average particle size: 0.45 - 0.62 mm, 1.6 liter), and the column is washed with water (10 liters). The materials adsorbed on the column are eluted with a 20% aqueous methanol (4 liters) and then with a 99% methanol (4 liters). The fraction eluted with the 99% methanol is concentrated under reduced pressure to give a residue (30 g). The residue is dissolved in a 99% methanol (300 ml) and the solution is introduced into a column (4.5 cm × 24 cm) of an activated alumina (400 g)., and the column is washed with water (1 liter) and then eluted with methanol-water (9 : 1 by volume, 2 liters) and then with methanol-water (1 : 1 by volume, 10 liters). The above procedure is repeated three times. The eluates with methanol-water (1 : 1 by volume) are combined and concentrated under reduced pressure to give crude sweetening fraction (33 g, on the basis of 1.5 kg of Fructus Momordicae). According to the TLC as described in Example 1, the fraction shows three spots which correspond to S-4, S-5 and S-6 in order of the height of Rf value (from the largest to the smallest).

The crude sweetening fraction is purified by a silica gel column chromatography as follows.

The crude sweetening fraction (30.5 g) is adsorbed onto Celite 535 (50 g) and the mixture is filled into a column (4.5 cm × 40 cm) of a silica gel (Wako Gel C-200, size: 100 - 200 mesh, 300 g) and developed with chloroform (2 liter) and then eluted wth mixed solvents of chloroform-methanol (the mixed ratio of the solvents is varied in order like 90 : 10, 80 : 20, . . . 60 : 40 by volume as shown in the following Table 3), wherein each 0.5 liter of the solvent is used in one elution. As the result, there are obtained the fractions as shown in Table 3.

Table 3

| Fraction No. | Solvent (mixed ratio by volume) | Amount of fraction (liter) |
|---|---|---|
| 1 | CHCl$_3$—MeOH (90 : 10) | 10.0 |
| 2 | CHCl$_3$—MeOH (80 : 20) | 5.0 |
| 3 | CHCl$_3$—MeOH (75 : 25) | 5.0 |
| 4 | CHCl$_3$—MeOH (75 : 25) | 5.0 |
| 5 | CHCl$_3$—MeOH (75 : 25) | 5.0 |
| 6 | CHCl$_3$—MeOH (75 : 25) | 2.5 |
| 7 | CHCl$_3$—MeOH (70 : 30) | 2.5 |
| 8 | CHCl$_3$—MeOH (70 : 30) | 5.0 |
| 9 | CHCl$_3$—MeOH (70 : 30) | 5.0 |
| 10 | CHCl$_3$—MeOH (60 : 40) | 5.0 |

According to TLC, the fractions 3 and 4 contains mainly S-4, the fractions 6 and 7 contains mainly S-5 and the fractions 8 and 9 contains mainly S-6.

The fractions 3 and 4 are combined and concentrated under reduced pressure to give crude S-4 (4.9 g). This crude product is adsorbed onto Celite 535 (about 30 g) and subjected repeatedly to a silica gel column chromatography (two to three times) until a single spot is observed on TLC. The material having a single spot on TLC is dissolved in a small amount of a 99% methanol and the insoluble materials are removed off. The mixture is concentrated and dried to give pure S-4 (about 3.5 g), melting point: 185° – 188° C (decomp.), $[\alpha]_D^{17}$ −4.2° (c=0.52, methanol).

Elementally analysis for C$_{54}$H$_{92}$O$_{24}$·2H$_2$O: Calcd (%): C,55.85, H,8.33 Found (%): C,55.47, H,8.41

EXAMPLE 6

The fractions 8 and 9 as obtained in Example 5 are combined and concentrated under reduced pressure to give crude S-6 (about 3.5 g). This crude product is purified likewise by a silica gel chromatography to give pure S-6 (about 450 mg), melting point: 198° –204° C (decomp.), $[\alpha]_D^{29}$ −4.2° (c=1.24, methanol).

Elementally analysis for C$_{66}$H$_{112}$O$_{34}$: Calcd (%): C,54.68, H,7.79 Found (%): C,54.64, H,7.79

EXAMPLE 7

A crude sweetening material obtained in the same manner as described in Example 5 is adsorbed onto Celite 535 (50 g) and the mixture is filled into a column (4.5 cm × 40 cm) of a silica gel (Wako Gel C-200, size: 100 – 200 mesh, 300 g) and developed with chloroform (2 liters) and then eluted with mixed solvents of chloroform-methanol in the mixed ratio of 75 : 25 by volume (10 liters), 70 : 30 by volume (10 liters) and 60 : 40 by volume (5 liters), wherein each 0.5 liter of the solvent is used in one elution.

According to TLC, the fraction by chloroform-methanol (60 : 40 by volume) contains mainly S-6. This fraction is concentrated under reduced pressure to givve crude S-6 (3.9 g). This crude S-6 is subjected repeatedly to a silica gel chromatography (two to three times), until a single spot is observed on TLC. The material having a singly spot on TLC is dissolved in a small amount of methanol and the insoluble materials are removed off. The mixture is concentrated and dried to give pure S-6, which has the same melting point and infrared spectrum as those of the product in Example 6.

EXAMPLE 8

In the same manner as described in Example 5, the fractions 6 and 7 obtained in the above Example 5 are combined and is subjected repeatedly to a silica gel chromatography (two to three times), until a single spot is observed on TLC, to give S-5.

This glycoside S-5 (6 g) is dissolved in a 0.005 M sodium dihydrogen phosphate buffer solution (pH 4.7, 1 liter), and thereto is added maltase (made by Sigma Co., 1 g). The mixture is stirred at 37° – 38° C for about 1 week, during which maltase is additionally added for several times (total amount of the maltase: 4 g). The reaction mixture is concentrated under reduced pressure so as to make about one third by volume, and extracted three times with n-butanol (200 ml). The extracts are combined and concentrated under reduced pressure to give hydrolysate mixture (3.7 g). Accordingly to TLC, it is confirmed that the hydrolysate mixture contains mainly S-1, S-2 and S-3.

the hydrolysate mixture (3.7 g) is adsorbed onto Celite 535 (10 g) and introduced into a column (3 cm × 28 cm) of a silica gel (Wako Gel C-200, size: 100 – 200 mesh, 75 g), and developed with chloroform (2 liters) and then eluted with chloroform-methanol (4 : 1 by volume, 4.5 liters), wherein each 400 ml of the solvent is used in one elution. According to TLC, the 2nd to 4th fractions contain mainly S-1, the 5th to 7th fractions contain mainly S-2, and the 8th to 10th fractions contain mainly S-3. These fractions are each subjected repeatedly to a silica gel chromatography (several times) until a single spot is observed on TLC to give pure S-1, S-2 and S-3, respectively.

The physical data of these products are shown in Table 4.

Table 4

| Product | Yield (g) | Melting point (° C) | $[\alpha]_D^{17}$ methanol | TLC Rf value A* | B** |
|---|---|---|---|---|---|
| S-1 | 0.7 | 265–266 | +41.0° (c=0.63) | 0.72 | 0.80 |
| S-2 | 0.6 | 187–195 | +20.0° (c=0.26) | 0.55 | 0.64 |
| S-3 | 0.4 | 184–188 | +6.7° (c=0.55) | 0.35 | 0.50 |

*A: chloroform-methanol-water (65 : 35 : 10 by volume)
**B: n-butanol-acetic acid-water (4 : 1 : 1 by volume)

Figure 7:
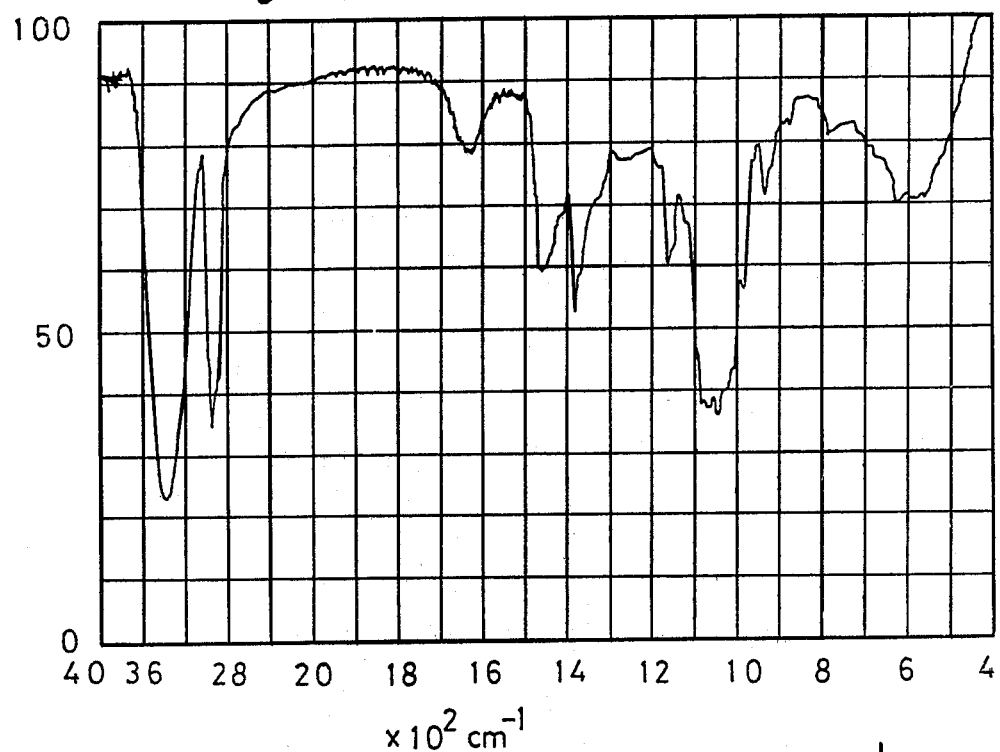
Figure 8:
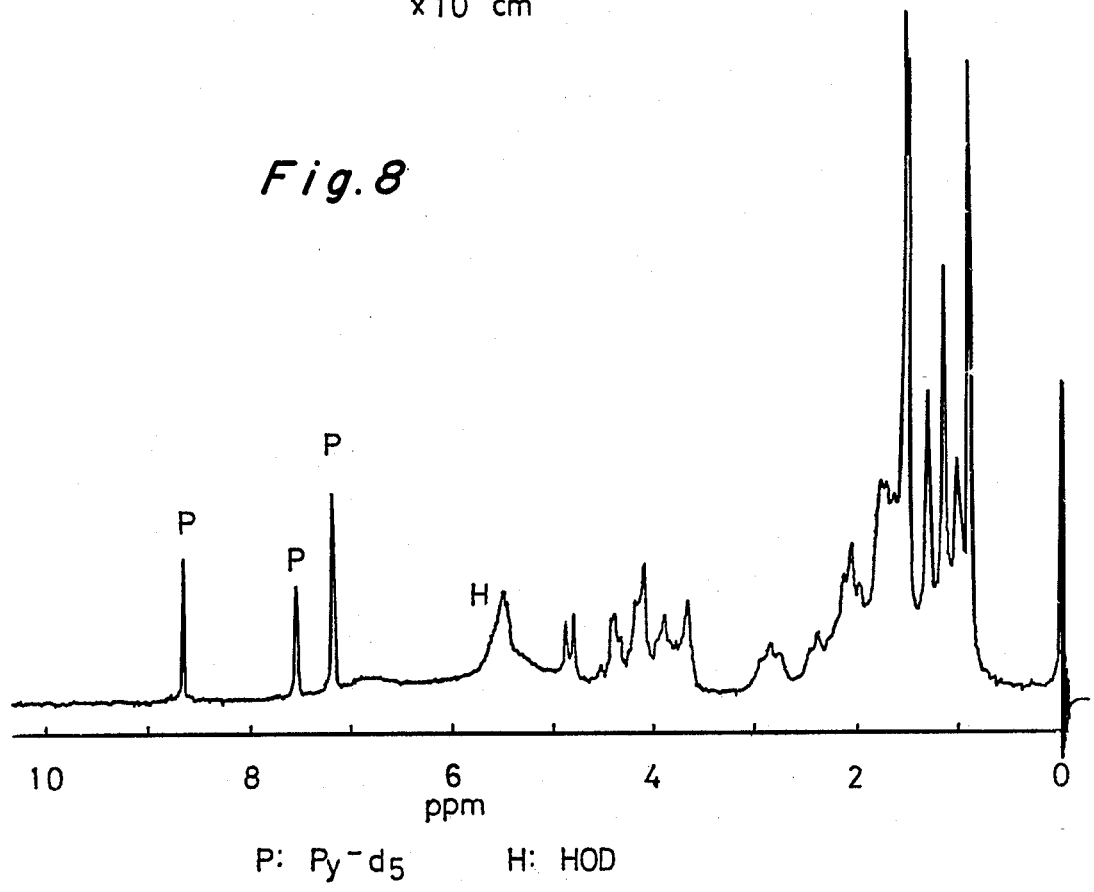
Figure 9:
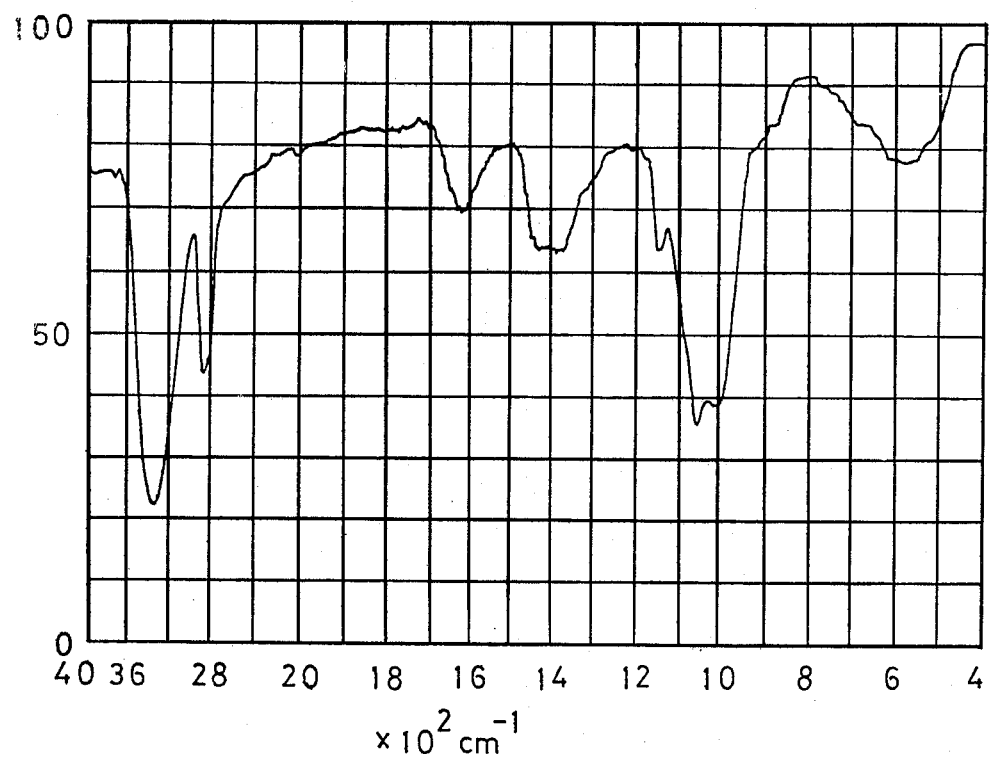
Figure 10:
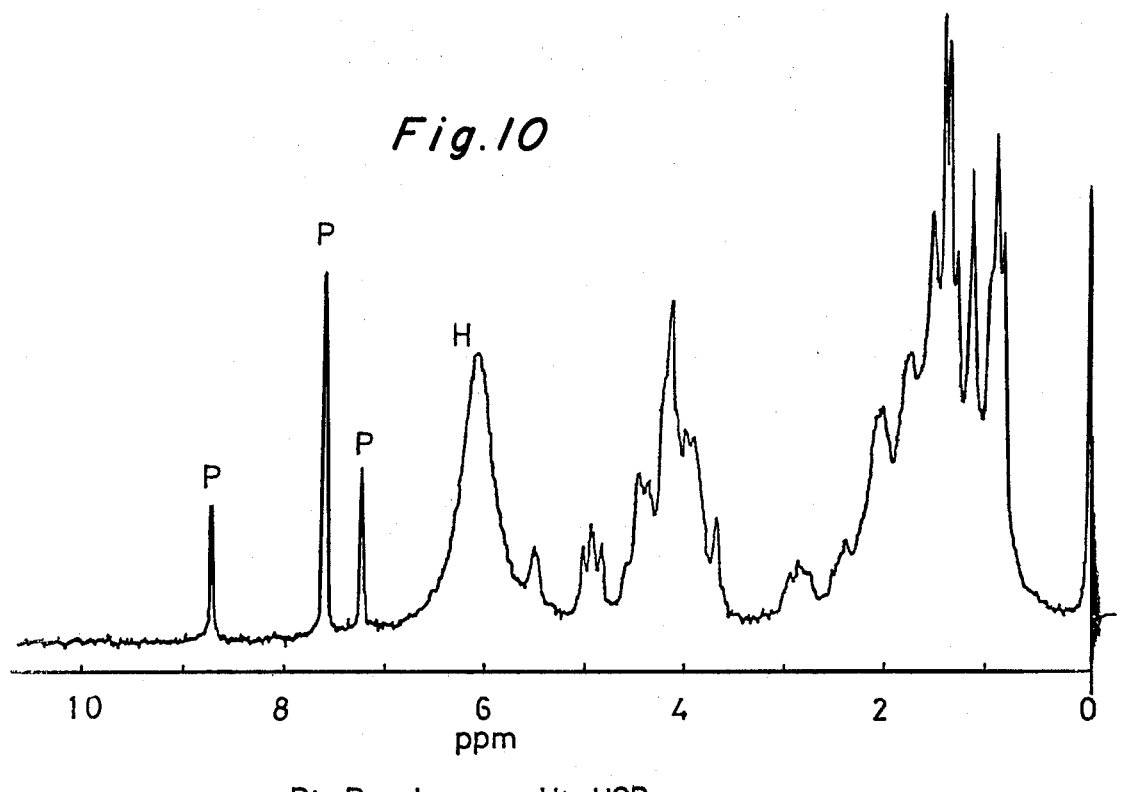
Figure 11:
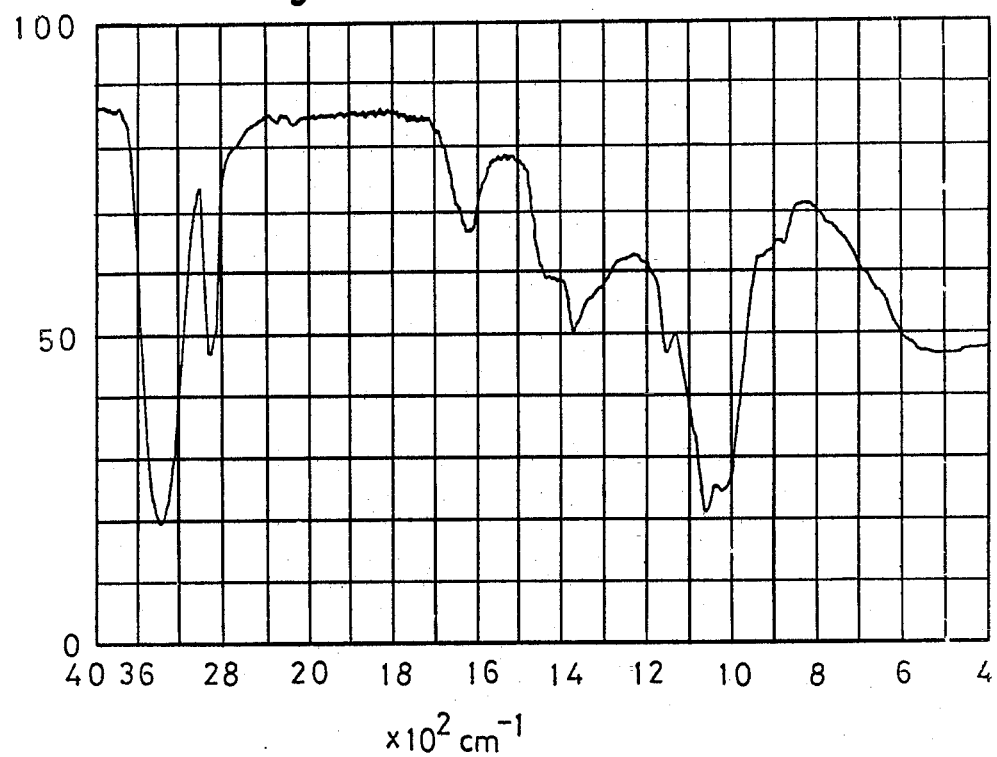
Figure 12:
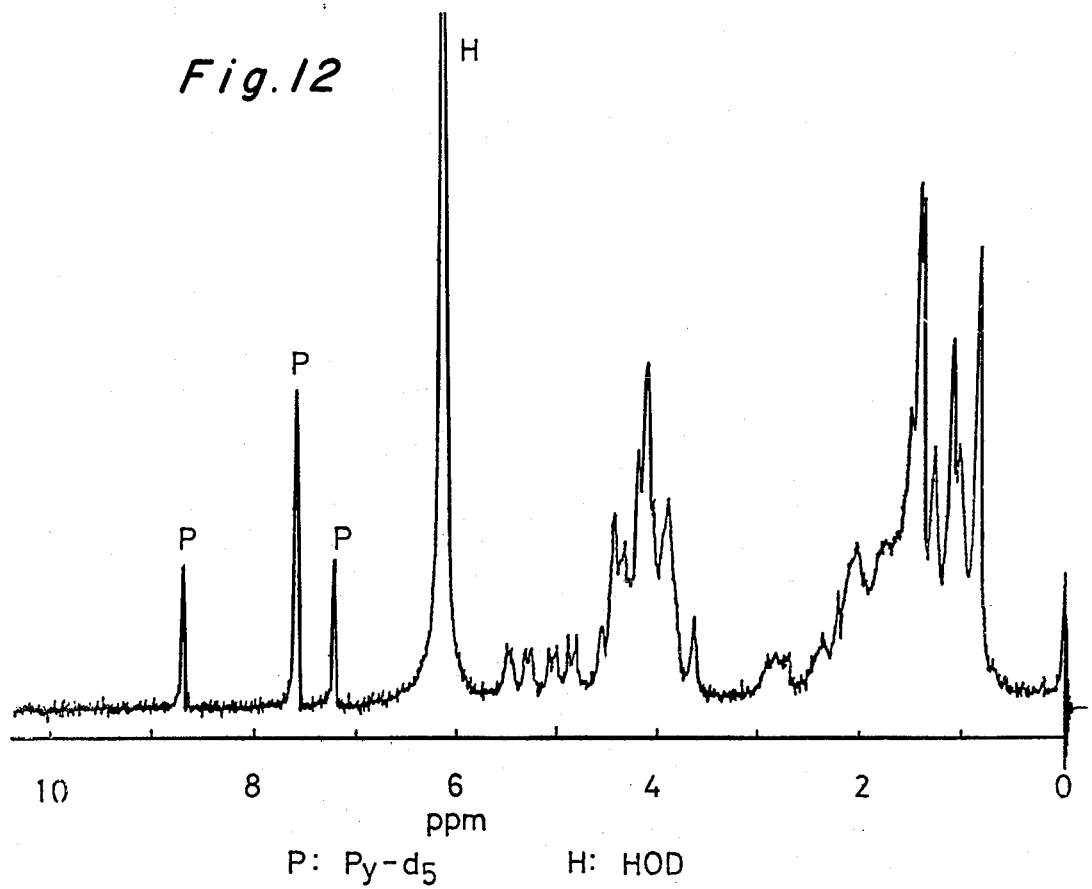

The infrared spectrum of these products are shown in FIG. 7 (S-1), FIG. 9 (S-2) and FIG. 11 (S-3), respectively, and the NMR spectrum of these products are shown in FIG. 8 (S-1), FIG. 10 (S-2) and FIG. 12 (S-3), respectively.

The elementally analysis of these products are shown in Table 5.

Table 5

| Product | Molecular formula | Calculated (%) | Found (%) |
|---|---|---|---|
| S-1 | C$_{36}$H$_{62}$O$_9$ | C,67.68; H,9.78 | C,67.27; H,9.78 |
| S-2 | C$_{42}$H$_{72}$O$_{14}$·3H$_2$O | C,58.99; H,9.20 | C,58.56; H,9.00 |
| S-3 | C$_{48}$H$_{82}$O$_{19}$·4H$_2$O | C,55.69; H,8.76 | C,55.69; H,8.51 |

EXAMPLE 9

In the same manner as described in Example 8, the glycoside S-5 (6 g) is hydrolysed with maltase for 2 hours and the hydrolysate is subjected to a silica gel chromatography to give pure S-4 (2 g). This product shows the same melting point and infrared spectrum as those of the product in Example 5.

EXAMPLE 10

The glycoside S-4 (400 mg) obtained in Example 9 is dissolved in a 95% ethanol (100 ml) and thereto are added a 0.005 M potassium dihydrogen phosphate buffer solution (the pH value is regulated with boric acid to about 3.4, 300 ml) and cellulase (grade II, made by Sigma Co, 1 g). The mixture is stirred at 37° C until the S-1 disappears (about one week), which is tested by TLC. After the reaction, the reaction mixture is concentrated under reduced pressure so as to make about 200 ml and then extracted three times with ethyl acetate 80 ml). The extracts are combined, washed with water and dried over anhydrous sodium sulfate, and then the solvent is destilled off to give an oily residue (about 300 mg). This oily residue is introduced into a column (2 cm × 10 cm) of a silica gel (Wako Gel C-200, 15 g) and developed and eluted with chloroform-acetone (100 : 5 by volume) to give crude S-0 (250 mg). This crude product is recrystallized from methanol-acetone to give pure S-0 (200 mg) as colorless needles, melting point: 118 – 119° C, $[\alpha]_D^{17}$ +70.0° (c=0.27, methanol).

Elementally analysis for $C_{30}H_{52}O_4 \cdot H_2O$: Calcd (%): C,72.83; H,11.00 Found (%): C,72.81; H,11.09

Figure 13:
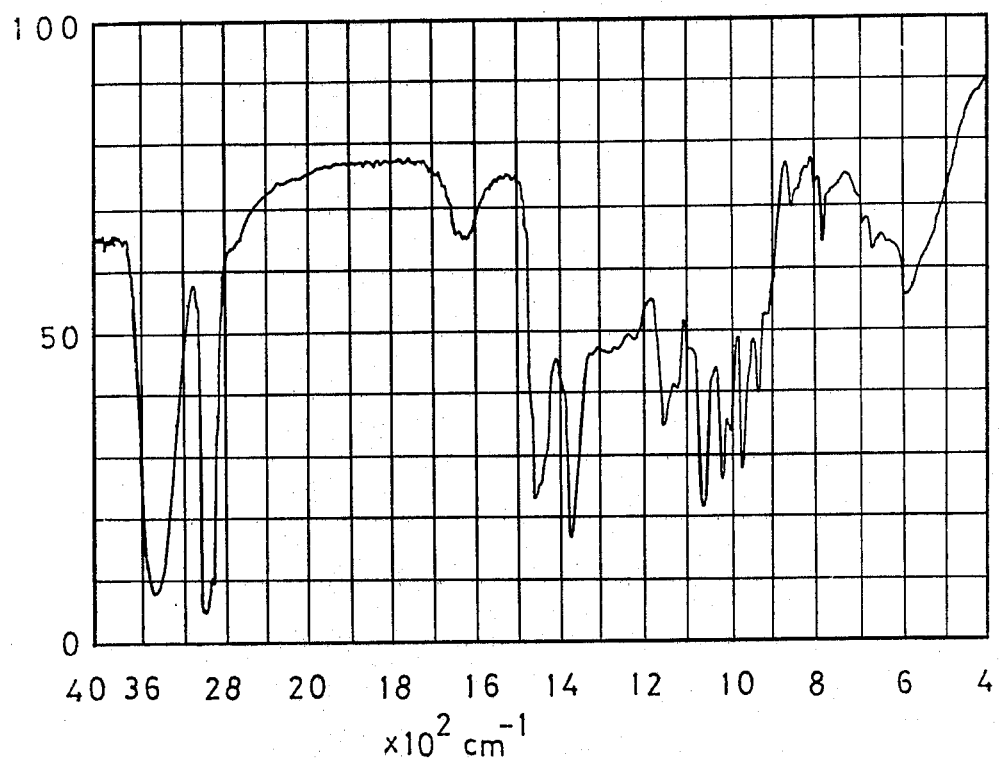
Figure 14:
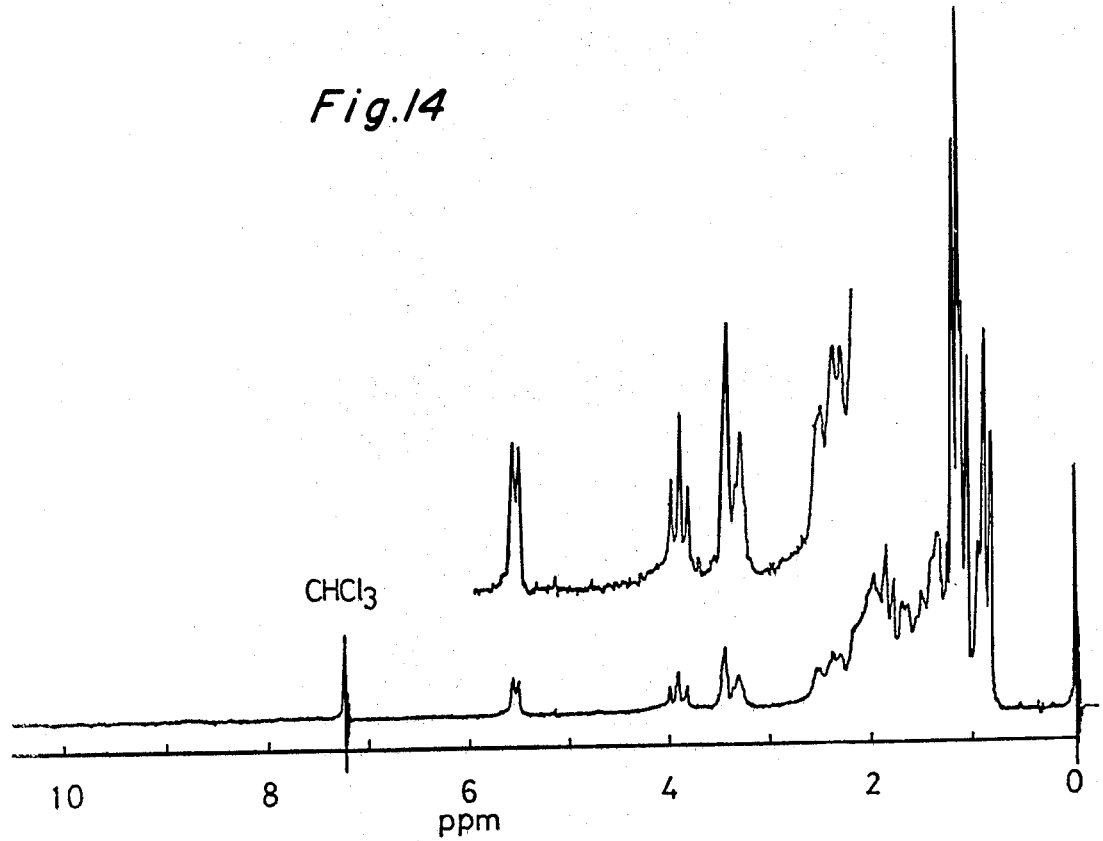

The infrared spectrum and NMR spectrum of this product are shown in FIG. 13 and FIG. 14, respectively.

EXAMPLE 11

The sweetness of S-6 obtained in Example 6 was tested as follows:

There were prepared a series of a standard sweetening agent: i.e. five series of an aqueous solution of fructose (2 g/100 ml, 3 q/100 ml, 4 g/100 ml, 5 g/100 ml and 6 g/100 ml). Separately, aqueous solution of S-6 (10 mg/100 ml and 20 mg/100 ml) were prepared.

The sweetness of the aqueous solution of S-6 was determined in comparison with that of the aqueous solution of fructose by using 10 panels, by which it was determined that the sweetness of the test solution corresponds to which series of the fructose solution. On the basis of the results, there were calculated the concentation of S-6 which showed the same sweetness as that of fructose (Relative to fructose value) and further the fold of sweetness of S-6 to that of fructose. The results are shown in Table 6.

Table 6

| Concentration of an aqueous solution of S-6 | Relative to fructose value of S-6 | The fold of sweetness of S-6 to that of fructose |
| --- | --- | --- |
| 10 mg/100 ml | 1.25 | 125 |
| 20 mg/100 ml | 2.50 | 125 |

EXAMPLE 12

S-5 (4 g) is dissolved in methanol (400 ml) and thereto is added a 10% methanol-HCl (50 ml). The mixture is refluxed from 5 hours and is neutralized with a 20% aqueous sodium hydroxide solution and then methanol is distilled off under reduced pressure. The resulting residue is extracted with n-butanol (100 ml) three times. The combined n-butanol layers are washed with water (100 ml) three times and then n-butanol is distilled off under reduced pressure to give a crude product containing mainly S-0 (1.7 g). What is claimed is:

1. A compound of the formula:

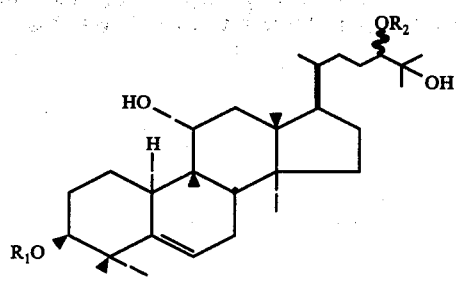

wherein $R_1$ and $R_2$ are the same or different and are each hydrogen, a residue of β-D-glucose, or a residue of an oligosaccharide comprising not more than four D-glucoses having 1,2- 1,4- and/or 1,6-bond, provided that the total number of the D-glucose residue in $R_1$ and $R_2$ is not more than 6 and provided that both $R_1$ and $R_2$ are not both hydrogen at the same time.

2. The compound according to claim 1, wherein $R_1$ is 6-(1-β-D-glucopyranosyl)-β-D-glucopyranosyl and $R_2$ is 2,6-bis(1-β-D-glucopyranosyl)-β-D-glucopyransoyl.

3. The compound according to claim 1, wherein $R_1$ is 6-(1-β-D-glucopyransoyl)-β-D-glucopyranosyl and $R_2$ is 2-(1-β-D-glucopyranosyl)-β-D-glucopyransoyl.

4. The compound according to claim 1, wherein $R_1$ and $R_2$ are each a residue of an oligosaccharide comprising not more than four β-D-glucoses having β-1,2- , β-1,4- and/or β-1,6-bond and the total number of the glucose residue in $R_1$ and $R_2$ is six.

5. The compound according to claim 1, wherein $R_1$ is 1-β-D-glucopyranosyl and $R_2$ is 2-(1-β-D-glucopyranosyl)-β-D-glucopyransoyl.

6. The compound according to claim 1, wherein $R_1$ and $R_2$ are each 1-β-D-glucopyransoyl.

7. The compound according to claim 1, wherein $R_1$ is 1-β-D-glucopyranosyl and $R_2$ is hydrogen.

8. A sweetening agent comprising a compound of the formula:

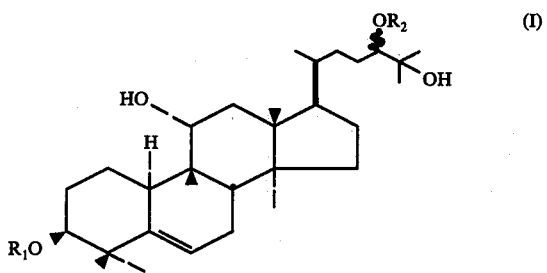

wherein $R_1$ and $R_2$ are the same or different and are each hydrogen, a residue of β-D-glucose, or a residue of an oligosaccharide comprising not more than four D-glucoses having 1,2-, 1,4- and/or 1,6-bond, provided that the total number of the D-glucose residue in $R_1$ and $R_2$ is 4 to 6, and a non-toxic carrier and provided that both $R_1$ and $R_2$ are not both hydrogen at the same time.

9. The sweetening agent according to claim 8, wherein said compound is a member selected from the group consisting of a compound of the formula (I) wherein $R_1$ is 6-(1-β-glucopyranosyl)-β-D-glucopyranosyl and $R_2$ is 2,6-bis(1-β-D- glucopyranosyl)-β-D-glucopyranosyl; a compound of the formula (I) wherein R₁ is 6-(1-β-D-glucopyranosyl)-β-D-glucopyranosyl and R₂ is 2-(1-β-D-glucopyranosyl)-β-D-glucopyranosyl; a compound of the formula (I) wherein R₁ and R₂ are each a residue of an oligosaccharide comprising not more than four β-D-glucoses having β-1,2-, β-1,4- and/or β-1,6-bond and the total number of the glucose residue in R₁ and R₂ is six; and a mixture of these three compounds.

* * * * *

UNITED STATES PATENT AND TRADEMARK OFFICE
CERTIFICATE OF CORRECTION

PATENT NO. : 4,084,010
DATED : April 11, 1978
INVENTOR(S) : Tsunematsu Takemoto et al.

It is certified that error appears in the above-identified patent and that said Letters Patent are hereby corrected as shown below:

In the Abstract, the formula should read:

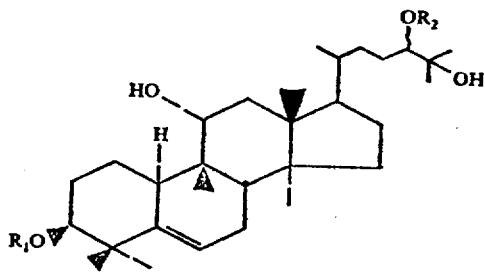

Signed and Sealed this

Fifth Day of December 1978

[SEAL]

Attest:

RUTH C. MASON
Attesting Officer

DONALD W. BANNER
Commissioner of Patents and Trademarks